(12) United States Patent
Yamashita et al.

(10) Patent No.: US 6,337,067 B1
(45) Date of Patent: Jan. 8, 2002

(54) WATER SOLUBLE DRY COMPOSITIONS

(75) Inventors: Chikamasa Yamashita, Naruto; Masaaki Odomi, Tokushima, both of (JP)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 09/486,277

(22) PCT Filed: Jun. 24, 1999

(86) PCT No.: PCT/JP99/03369

§ 371 Date: Feb. 25, 2000

§ 102(e) Date: Feb. 25, 2000

(87) PCT Pub. No.: WO00/00221

PCT Pub. Date: Jan. 6, 2000

(30) Foreign Application Priority Data

Jun. 26, 1998 (JP) ............................................. 10-180796

(51) Int. Cl.[7] ............................ A61K 45/00; C07K 1/00
(52) U.S. Cl. ........................ 424/85.2; 424/85.1; 530/351
(58) Field of Search .............................. 424/85.2, 85.1; 530/351

(56) References Cited

U.S. PATENT DOCUMENTS 5,919,443 A * 7/1999 Michaelis et al. ......... 424/85.1

FOREIGN PATENT DOCUMENTS

| EP | 0 168 008 A2 | 1/1986 |
| JP | 8-504784 | 5/1996 |
| WO | WO 97/23239 | 7/1997 |

* cited by examiner

Primary Examiner—Jezia Riley
(74) Attorney, Agent, or Firm—Sughrue Mion, PLLC

(57) ABSTRACT

Provisions of a foam inhibitor which effectively inhibits foaming (bubbling) caused at the time of dissolving dry compositions and of a water-soluble dry composition which comprises the foam inhibitor. The form inhibitor is suitable for inhibiting foaming caused at the time of dissolving dry compositions comprising saccharide which contain a hydrophobic amino acid as essential ingredient; and the water-soluble dry composition contains pharmacologically active proteinaceous substance, saccharide and hydrophobic amino acid having the hydropathy index of about not less than 2, wherein the concentration of the hydrophobic amino acid is in the range of 0.05 wt. % to less than 40 wt. % based on the total amount of the dry composition.

23 Claims, No Drawings

WATER SOLUBLE DRY COMPOSITIONS

This is a Rule 371 of PCT/JP99/03369 application, filed on Jun. 24, 1999 designating the United States, the disclosure of which is incorporated herein by reference.

TECHNICAL FIELD

The present invention relates to a foam inhibitor which effectively inhibits foaming (bubbling) caused when dissolving a dry composition and to a water-soluble dry composition which comprises the foam inhibitor so that foaming (bubbling) is significantly inhibited.

BACKGROUND ART

In dry compositions containing pharmacologically active proteinaceous substances as active ingredients, various saccharides including sucrose have conventionally been used as stabilizer for the active ingredients (see Japanese Unexamined Patent Publications Nos. 92619/1983, 48933/1985 and 138222/1990).

The conventional dry compositions of pharmacologically active proteinaceous substances containing saccharides, however, tend to foam severely when dissolved at the time of utilization depending on the amount of saccharides contained therein. The foaming may cause problems such as erroneous assessment or identification of insoluble foreign matters, introduction of bubbles into a syringe together with solution in preparing an injection solution, a longer time required for the preparation of the solution, etc.

Further, in the case where solutions of medical compositions containing saccharides are freeze-dried, the freeze-dried cakes obtained are prone to shrinkage, resulting in deterioration of appearances of drugs. Moreover, if an excessive amount of saccharides is blended in a preparation, a relatively long time is unavoidably required for the freeze-drying.

DISCLOSURE OF INVENTION

An object of the present invention is to provide a foam inhibitor which effectively inhibits foaming caused when dissolving a conventional dry composition containing a saccharide. Another object of the present invention is to provide a dry composition wherein the foaming usually observed at the time of redissolving the dry compositions is effectively inhibited.

The inventors have conducted an extensive study to achieve the above objects. Consequently, the inventors have found that a group of amino acids have characteristics to effectively inhibit the foaming associated with the dissolving of the conventional dry compositions containing saccharides, especially, the dry compositions containing saccharides and pharmacologically active proteinaceous substances, and that a desired dry composition which is free of the above-mentioned problems can be prepared by utilizing the amino acids as foam inhibitor.

The present invention has been accomplished based on the above findings.

Specifically, the present invention provides a foam inhibitor containing hydrophobic amino acid as essential ingredient which is suitable for inhibiting foaming usually observed when dissolving a conventional dry composition containing a saccharide. The foam inhibitors of the invention include the following modes of embodiments.

1. A foam inhibitor comprising a hydrophobic amino acid having a hydropathy index of any one of the following values of not less than 2, not less than 2.8, not less than 3.8 or 3.8–4.5.
2. A foam inhibitor wherein the hydrophobic amino acid is at least one species selected from the group consisting of valine, leucine, isoleucine and phenylalanine.
3. A form inhibitor wherein the concentration of hydrophobic amino acid is in the range of 1–100 wt. % based on 100 wt. % of saccharide contained in the dry composition.
4. A foam inhibitor wherein the saccharide is at least one species selected from the group consisting of sucrose, maltose, lactose, trehalose, mannitol, xylitol, dextran and chondroitin sulfate.
5. A foam inhibitor whose object dry composition is a freeze-dried composition.

The present invention further provides a water-soluble dry composition containing a pharmacologically active proteinaceous substance, saccharide and hydrophobic amino acid having a hydropathy index of about not less than 2, wherein the concentration of the hydrophobic amino acid is from 0.05 wt. % to less than 40 wt. % based on the total amount of dry composition. The water-soluble dry compositions of the invention include the following modes of embodiments.

a. A water-soluble dry composition wherein a hydrophobic amino acid has a hydropathy index of any one of the values of not less than 2.8, not less than 3.8 or 3.8–4.5.
b. A water-soluble dry composition wherein the saccharide is at least one species selected from the group consisting of sucrose, maltose, lactose, trehalose, mannitol, xylitol, dextran and chondroitin sulfate.
c. A water-soluble dry composition which comprises at least one pharmacologically active substance selected from the group consisting of antiviral polypeptides, immunomodulator polypeptides and hematinic polypeptides.
d. A water-soluble dry composition wherein the pharmacologically active substance is at least one species selected from the group consisting of antiviral polypeptides, immunomodulator polypeptides and hematinic polypeptides, and the saccharide is at least one species selected from the group consisting of disaccharides, sugar alcohols and polysaccharides.
e. A water-soluble dry composition wherein the concentration of the hydrophobic amino acid is in the range of 1–10 wt. % based on 100 wt. % of the saccharide contained in the water-soluble dry composition.
f. A water-soluble dry composition wherein the concentration of hydrophobic amino acid is in the range of 0.1–30 wt. % based on the total amount of the dry composition.
g. A water-soluble dry composition wherein the concentration of the hydrophobic amino acid is in the range of 2–50 wt. % based on 100 wt. % of the saccharide.
h. A water-soluble dry composition wherein the concentration of the hydrophobic amino acid is in the range of 0.5–30 wt. % based on the total amount of the dry composition.
i. A water-soluble dry composition wherein the pharmacologically active substance is at least one species selected from the group consisting of antiviral polypeptides, immunomodulator polypeptides and hematinic polypeptides, and the saccharide is at least one species selected from the group consisting of disaccharides, sugar alcohols and polysaccharides.

j. A water-soluble dry composition wherein the pharmacologically active proteinaceous substance is interleukin and/or interferon, and the saccharide is disaccharide.

k. A water-soluble dry composition wherein the dry composition is a freeze-dried composition.

l. A water-soluble dry composition which is substantially free of human serum albumins, but contains polar amino acid having a hydropathy index of not more than 0 and surfactant.

According to the invention, it is possible to effectively inhibit foaming prone to occur when dissolving a dry composition containing saccharide and to prepare a solution excellent in clarity. Further, even in the case where lyophilization is employed as drying step, it is possible to effectively prevent shrinkage of the freeze-dried cakes, thereby obtaining dry products excellent in the appearance.

Moreover, in the dry compositions of the invention, especially in the freeze-dried products, the moisture content is satisfactorily reduced in a shorter drying time than that required for the conventional freeze-dried products which do not contain hydrophobic amino acid having a hydropathy index of not less than about 2. Thus, the present invention enables to reduce the drying time in the whole process of preparing a dry composition, which is advantageous in the industrial production.

The invention will hereinafter be described in more detail.

(1) Foam Inhibitor

The present invention provides a foam inhibitor which contains hydrophobic amino acid as essential ingredient. The foam inhibitor has the characteristics of effectively inhibiting foaming usually induced at the time of dissolving a dry composition, especially a dry composition containing saccharide.

The hydrophobic amino acids to be used in the invention are those having the hydropathy index of at least about 2 (see "A Simple Method for Displaying the Hydropathic Character of a Proteins", Jack Kyte and Russel F. Doolittel, J. Mol. Biol., (1982)157, 105–132). Any amino acids having the above physical property may be used in the invention whether or not they are protein-constituting amino acids. The amino acids may preferably be those having a hydropathy index of about 2.8 or larger such as valine, leucine, isoleucine and phenylalanin; more preferably those having a hydropathy index of about 3.8 or larger such as valine, leucine and isoleucine; and further more preferably those having a hydropathy index of about 3.8–4.5 such as leucine.

The hydrophobic amino acids to be used in the invention may be in the form of dipeptides, tripeptides, salts or amides. Examples of the dipeptides of hydrophobic amino acids include leucyl-valine, isoleucyl-valine, isoleucyl-leucine, leucyl-glycine, etc. Examples of the tripeptides of hydrophobic amino acids include isoleucyl-leucyl-valine, leucyl-glicyl-glycine, etc. Examples of the salts of hydrophobic amino acids include a salt thereof with an alkali metal such as a sodium, potassium, etc. or with an alkali earth metal such as a calcium, etc.; and an adduct salt thereof with an inorganic acid such as a phosphoric acid, hydrochloric acid, etc. or with an organic acid such as a sulfonic acid, etc. More specific examples of the salts of hydrophobic amino acids include an L-leucic amide hydrophobic acid salt, L-isoleucyl-β-naphthylamide hydrobromide, L-valine-β-naphthylamide, etc.

These hydrophobic amino acids (including those in a form of a salt or amide) may be used alone, but two or more kinds thereof may be used in combination.

Object of the foam inhibitors of the invention is dry compositions containing saccharides.

The saccharides to be used in the invention are not limited, and examples thereof include those conventionally used as stabilizers or the like for the dry medical compositions, especially for the medical compositions containing pharmacologically active proteinaceous substances. More specifically, examples of the saccharides include disaccharides such as sucrose, maltose, lactose, trehalose, etc.; sugar alcohols such as mannitol, xylitol, etc.; and polysaccharides such as dextran 40, dextran 70, chondroitin sulfate, etc. These saccharides may be contained in a dry composition alone, but two or more kinds thereof may be used in combination. Preferable saccharides to be used in the invention are disaccharides such as sucrose, maltose, lactose, trehalose, etc.; among which sucrose is more preferable.

Concentrations of the saccharides in the dry composition are not limited as long as foaming is caused by dissolving the conventional dry compositions. Specifically, though the concentrations vary depending on the kind of saccharide to be contained, the concentration of a disaccharide such as sucrose, for example, may be usually 10–90 wt. %, in some cases 20–80 wt. % or in some cases 40–80 wt. % based on 100 wt. % of the dry composition.

The foam inhibitors of the invention are suitably used for the dry compositions that contain pharmacologically active proteinaceous substances as the active ingredients.

The pharmacologically active proteinaceous substances to be used in the invention may be proteins or peptides (including a polypeptide) having pharmacological activities, and examples thereof include proteins such as enzyme, hemoglobin, immunoglobulin, hormone, blood coagulation factor, etc.; and polypeptides such as antiviral polypeptides (ex. interferons-α, -β, -γ, etc.), immunomodulator polypeptides (ex. interleukins-1, 2, 3, 4, 5, 6, 7, 8, etc.), hematinic polypeptides (ex. erythropoietin, granulocyte colony stimulating factor, macrophage-colony stimulating factor and granulocyte-macrophage-colony stimulating factor), etc. These polypeptides may be contained in the dry composition alone, but two or more kinds thereof may be used in combination.

The above proteins and peptides respectively include those existing in nature, produced by gene recombinant technique or chemical syntheses.

The concentration of the pharmacologically active proteinaceous substance in the dry composition is not limited. Specifically, examples of the concentration may be, though the concentration varies depending on the kind of the pharmacologically active proteinaceous substance to be used, typically not more than 20 wt. %, in some cases 0.00001–10 wt. %, in some cases 0.0001–10 wt. %, in some cases 0.001–10 wt. % and in some cases 0.001–5 wt. % based on 100 wt. % of the dry composition.

The object dry compositions of the foam inhibitors of the invention may further contain human serum albumins, polar amino acids or salts thereof (ex. amino acids having the hydropathy index of not more than 0 or salts thereof), inorganic salts, gelatins, surfactants, a buffers, etc.

Methods of utilizing the foam inhibitors of the invention are not limited, and the foam inhibitors may be used in such a manner that they are contained in the dry compositions at the time of dissolving (redissolving) the compositions. Usually, the foam inhibitor of the invention is added to a solution containing a.saccharide and/or pharmacologically active proteinaceous substance in advance of preparing a dry composition (dried product) or added to a solution together with a saccharide and pharmacologically active proteinaceous substance.

The concentration of the foam inhibitor in the dry composition is not limited, but may be in the range of, as the concentration of the hydrophobic amino acid based on 100 wt. % of the dry composition, typically from 0.05 to less than 40 wt. %, preferably about 0.1–30 wt. %, more preferably about 0.5–30 wt. %, more preferably about 1–25 wt. %, further more preferably about 2–20 wt. %.

The concentration of the hydrophobic amino acid per 100 wt. % of the saccharide in the dry composition, as the hydrophobic amino acid, is in the range of usually about 1–100 wt. %, preferably about 2–50 wt. %, more preferably about 3–25 wt. %.

(2) Water-Soluble Dry Composition

The present invention further provides a water-soluble dry composition containing the above-described foam inhibitor. Specifically, the water-soluble dry composition of the invention contains at least a pharmacologically active proteinaceous substance, saccharide and hydrophobic amino acid.

Examples of the pharmacologically active proteinaceous substance include various proteins and peptides (including polypeptides) as described above. Preferable pharmacologically active proteinaceous substances are interleukin 1, 2, 3, 4, 5, 6, 7 or 8 of the immunomodulator polypeptides, interferons-$\alpha$, -$\beta$ or -$\gamma$ of the antiviral polypeptides and erythropoietin, granulocyte colony stimulating factor, macrophage-colony stimulating factor and granulocyte-macrophage-colony stimulating factor of the hematinic polypeptides. These pharmacologically active proteinaceous substances may be contained in the dry compositions alone, but two or more kinds thereof may be used in combination.

The concentration of the pharmacologically active proteinaceous substance in the water-soluble dry composition is as described above; however, the concentration may be changed depending on the diseases, drug administration forms, etc., so that clinically optimum amounts thereof may be contained. Content of an interleukin or of an interferon in the total amount of the dry composition may be, for example, 1–10×$10^9$ IU/mg, preferably 1–10×$10^8$ IU/mg, more preferably 1–10×$10^7$ IU/mg, 10–8×$10^7$ IU/mg in some cases, 100–6×$10^7$ IU/mg in some cases, 100–4×$10^7$ IU/mg in some cases, 100–3×$10^7$ IU/mg in some cases, 100–2×$10^7$ IU/mg in some cases, 100–1×$10^7$ IU/mg in some cases, 100–2×$10^8$ IU/mg in some cases.

Saccharides to be used in the invention are not limited as long as they may typically be employed as stabilizers or the like for the medical compositions which contain pharmacologically active proteinaceous substances, and examples thereof include various saccharides as described above. Preferable saccharides are disaccharides such as sucrose, maltose, lactose, trehalose, etc.; among which the sucrose is more preferable. These saccharides are blended with the dry compositions alone, but two or more kinds thereof may be used in combination. In addition, the concentration of the saccharide in the dry composition is not limited, and examples thereof include those of mentioned above.

Examples of the hydrophobic amino acid include, as described above, those having a hydropathy index of about 2 or larger, preferably of about 2.8 or larger such as valine, leucine, isoleucine and phenylalanine; those having a hydropathy index of about 3.8 or larger such as valine, leucine and isoleucine; and those having a hydropathy index of about 3.8–4.5 such as leucine. The hydrophobic amino acids specified above may work as foam inhibitors for saccharides-containing dry compositions. The hydrophobic amino acids may be contained in the dry compositions alone, but two or more kinds thereof may be used in combination. In addition, the concentration of the hydrophobic amino acid in the dry composition is not limited, and the examples thereof may be as described above i.e. in the range of 0.05 wt. % to not more than 40 wt. %, preferably about 0.1–30 wt. %, about 0.5–30 wt. % in some cases, about 1–25 wt. % in some cases, and about 2–20 wt. % in some cases.

The concentration of the hydrophobic amino acid per 100 wt. % of the saccharide in the dry composition, as the hydrophobic amino acid, is in the range of usually about 1–100 wt. %, preferably about 2–50 wt. %, more preferably about 3–25 wt. %.

Known materials as stabilizers, etc., such as human serum albumins, polar amino acids having the hydropathy index of not more than 0 (including those in a form of a salt or amide), inorganic salts, gelatins, surfactants, buffers, or the like may be contained in the dry compositions of the invention alone, but two or more kinds thereof may be used in combination for the purposes of stabilizing the solution before drying, stabilizing the dry composition after drying and/or of prevention of the active ingredients from being adsorbed to a vessel, etc.

The human serum albumin is not always necessary in the invention; however, in the case where it is contained in the dry composition, the concentration is in the range of, for example, typically more than 0 and not more than 30 wt. %, not more than 20 wt. % in some cases and not more than 10 wt. % in some cases, based on 100 wt. % of the dry composition.

In the case where the human serum albumin is not added with the dry composition, it is preferable to add at least one species selected from the polar amino acids having hydropathy index of not more than 0 (including those in a form of a salt or an amide), gelatins, surfactants, etc.

Examples of the polar amino acids having the hydropathy index of not more than 0 include glycine, proline, alanine, arginine, glutamic acid. These polar amino acids may be used alone, but two or more kinds thereof may be used in combination. The polar amino acids further include those in the form of a salt or amide. Examples of the salt of the polar amino acid include a salt thereof with an alkali metal such as a sodium, potassium, etc. or with an alkali earth metal such as a calcium, etc.; and an adduct salt thereof with an inorganic acid such as a phosphoric acid, hydrochloric acid, etc. or with an organic acid such as a sulfonic acid, etc.

Examples of preferable polar amino acids are glycine, proline, arginine, glutamic acid and salts thereof, more specifically, glycine, arginine hydrochloride and sodium glutamate.

The concentration of the polar amino acid is not limited, for example, the range of typically 0.1–50 wt. %, in some cases 0.5–30 wt. %, in some cases 1–20 wt. %, based on 100 wt. % of the dry composition.

As the surfactant, various surfactants utilized in the typical pharmaceutical preparations, such as anionic surfactants, cationic surfactants, nonionic surfactants and dipolar surfactants may be used in the present invention. Examples of suitable surfactants include nonionic surfactants such as a polyoxyethylenesorbitan aliphatic ester (ex. Tween-type surfactants), sorbitantriolate, etc. Herein, the surfactant may be added in the dry composition depending on the kind of pharmacologically active proteinaceous substance in the dry composition, i.e. the surfactant may be unnecessary depending on the kind of pharmacologically active proteinaceous substance in the dry composition. In the case where the surfactant is required, the concentration of the surfactant in the dry composition may be in the range of typically 0.0001–20 wt. %, in some 0.001–10 wt. % cases, and in some cases 0.001–5 wt. %.

Buffers to be used in the invention may be those having the buffer capacity in the range of pH values of pH 6–8, preferably of pH 6.5–8, so that a solution of the dry composition has pH values suitable for injection. Buffers typically used for injection are employed, including organic acid-based and inorganic acid-based buffers. The preferable buffers are organic acid-based buffers such as a citrate buffer.

The dry composition of the invention is prepared by any drying methods (ex. spray drying, lyophilization, etc.) without particular limitations.

Specifically, taking the lyophilization as an example, the dry composition of the present invention can be prepared by dissolving a composition containing at least a pharmacologically active proteinaceous substance, saccharide and hydrophobic amino acid at the above-described concentrations into a solution for medical preparation, followed by freeze-drying the solution by the usual lyophilization method.

The water-soluble dry composition of the invention is dissolved at the time of utilization typically by adding water for injection (distilled water or sterilized water) thereto. Foaming is usually caused in the case where conventional dry composition which contains no hydrophobic amino acid is dissolved; however, in the present invention, the foaming is effectively inhibited so that the injection solution of high clarity is prepared. Accordingly, entering of an insoluble foreign matters is assessed without mistake, and, since the foaming is not practically caused, entering of bubbles into a syringe at the time of sucking the solution into the syringe is assuredly prevented.

The shrinkage of freeze-dried cake which is typically caused by the absence of hydrophobic amino acid is effectively suppressed in the present invention even though the water-soluble dry composition is prepared by lyophilization, so that the improvement in appearances of drugs is achieved. Further, blending of the hydrophobic amino acid with a pharmacologically active proteinaceous substance containing saccharide produce an effect of significantly reducing the time required for freeze-drying compared to the case wherein no hydrophobic amino acid is blended in the preparation of dry composition. This effect is remarkable especially when a disaccharide such as sucrose and a buffer such as a citrate buffer are contained in the preparation.

Consequently, in view of the above-described effects, the preferable water-soluble dry compositions of the invention are the freeze-dried compositions prepared by the lyophilization.

BEST MODE FOR CARRYING OUT THE INVENTION

The present invention will hereinafter be illustrated more in detail with reference to the following Examples. Note that the present invention is not limited at all by the Examples. The abbreviations described in the Examples are as defined in the following:

IFN: interferon:

IL: interleukin;

G-CSF: granulocyte colony stimulating factor.

EXAMPLES 1 TO 4

In each Examples, a mixture was prepared in such a manner that 0.25 ml of an IFN-α solution (titer: $2 \times 10^7$ IU/ml), 40 mg of sucrose and 5 mg of an amino acid (see Table 1 for each prescriptions) are mixed per 1 vial (1 ml of capacity) by dissolving them by adding a suitable amount of distilled water for injection. The mixture was freeze-dried using the lyophilizer comprising shelves (LYOVAC GT-4: LEYBOLD) following the method described below.

<Freeze-Drying Method>
1. The shelves were subjected to quick cooling so that the shelf temperature is reduced to −40° C.
2. Loading the vials onto cooled shelves in a freeze-drying chamber to freeze the mixtures in the vials.
3. The shelf temperature of −40° C. was maintained for three hours, and then a pressure reduction was started.
4. After the pressure was reduced to 0.1 mbar, the temperature of the shelf was elevated up to 20° C. expending 2 hours, and then the conditions were maintained for succeeding 8 hours.
5. The shelf temperature was elevated up to 40° C. expending 30 minuets, followed by a further pressure reduction, and then the conditions were maintained for 2 hours.
6. The shelf temperature was reduced to 25° C. expending 30 minutes, and then the conditions were maintained for 1 hour to complete the freeze-drying.

The appearances of the freeze-dried samples were observed as well as the formability by dissolving the samples with 1 ml of the distilled water for injection. Results are shown in Table 1.

TABLE 1

| | | Preparation | Hydropathy Index of Amino Acids | Shrinkage | Foamability |
|---|---|---|---|---|---|
| Example | 1. | IFN-α + sucrose + isoleucine | 4.5 | ± | ± |
| | 2. | IFN-α + sucrose + valine | 4.2 | ± | ± |
| | 3. | IFN-α + sucrose + leucine | 3.8 | ± | ± |
| | 4. | IFN-α + sucrose + phenylalanine | 2.8 | + | + |
| Comp. Examples | 1. | IFN-α + sucrose | — | +++ | +++ |
| | 2. | IFN-α + sucrose + glycine | −0.4 | ++ | +++ |
| | 3. | IFN-α + sucrose + proline | −1.6 | ++ | +++ |
| | 4. | IFN-α + sucrose + arginine hydrochloride | −4.5 | +++ | +++ |

The shrinkage and foamability were evaluated in accordance with the following criteria:

Shrinkage:
±freeze-dried cake was very slightly shrinked.
+freeze-dried cake was slightly shrinked.
++freeze-dried cake was considerably shrinked.
+++freeze-dried cake was exceedingly shrinked.

Foamability:
±very slight foaming.
+a slight foaming.
++considerable foaming.
+++exceeding foaming.

As is apparent from Table 1, the foamabilities of the freeze-dried cakes containing sucrose at the time of dissolving were effectively suppressed by using the hydrophobic amino acids having the hydropathy index of not less than 2, and the appearances of the product were considerably improved as a result of suppression of the shrinkage.

EXAMPLES 5–8

Freeze-dried compositions were obtained in the same manner as that described in Examples 1–4, except for using 0.25 ml of IL-1α solution (titer: $2 \times 10^8$ IU/ml) in place of the IFN-α solution.

EXAMPLES 9–12

Freeze-dried compositions were obtained in the same manner as that described in Examples 1–4, except for further adding 1 mg of a nonionic surfactant (Tween 80).

EXAMPLES 13–16

Freeze-dried compositions were obtained in the same manner as that described in Examples 1–4, except for further adding 3 mg of glycine which is a polar amino acid.

EXAMPLES 17–20

Freeze-dried compositions were obtained in the same manner as that described in Examples 1–4, except for using 0.25 ml of IFN-γ solution (titer: $2 \times 10^7$ IU/ml) in place of the IFN-α bulk solution and adding the 30 mM citrate buffer solution as a buffer.

EXAMPLES 21–24

Freeze-dried compositions were obtained in the same manner as that described in Examples 1–4, except for using 40 mg of trehalose in place of 40 mg of sucrose.

EXAMPLES 25–28

Freeze-dried compositions were obtained in the same manner as that described in Examples 1–4, except for adding to each Examples 1 mg of Tween 80, 3 mg of glycine and 30 mM citrate buffer solution as a buffer.

EXAMPLES 29–32

Freeze-dried compositions were obtained in the same manner as that described in Examples 25–28, except for using 60 mM phosphate buffer in place of the 30 mM citrate buffer solution, as a buffer.

EXAMPLES 33–36

Freeze-dried compositions were obtained in the same manner as that described in Examples 25–28, except for using 0.1 mg of Pluronic F-68 (aka: polyoxyethylene(160) polyoxypropylene(30)glycol; Trade Name: Adekapluronic F-68; Asahi Denka Kogyo K.K.) in place of 1 mg of the Tween 80.

EXAMPLES 37–40

Freeze dried compositions were obtained in the same manner as that described in Examples 1–4, except for changing the amount of sucrose from 40 mg to 50 mg, and adding 0.1 mg of Tween 80 and 30 mM citrate buffer solution.

EXAMPLE 41

A freeze-dried composition was obtained in the same manner as that described in Example 1, except for adding 5 mg of valine, 0.1 mg of Tween 80, and 30 mM citrate buffer solution.

EXAMPLE 42

A freeze-dried composition was obtained in the same manner as that described in Example 3, except for adding 5 mg of valine, 0.1 mg of Tween 80 and 45 mM citrate buffer solution.

EXAMPLES 43–46

Freeze-dried compositions were obtained in the same manner as that described in Examples 25–28, except for using 25 mg of D-mannitol in place of 40 mg of sucrose.

EXAMPLE 47

A freeze-dried composition was obtained in the same manner as that described in Example 2, except for changing the amount of valine from 5 mg to 15 mg, and adding 1 mg of Tween 80 as well as 25 mM citrate buffer solution.

EXAMPLE 48

A freeze-dried composition was obtained in the same manner as that described in Example 3, except for changing the amount of leucine from 5 mg to 3 mg, and adding 1 mg of Tween 80, 5 mg of glycine and 30 mM citrate buffer solution.

EXAMPLES 49–52

Freeze-dried compositions were obtained in the same manner as that described in Examples 17–20, except for adding 1 mg of Tween 80 and 3 mg of glycine.

EXAMPLES 53–56

Freeze-dried compositions were obtained in the same manner as that described in Examples 43–46, except for using 60 mM phosphate buffer solution in place of the 30 mM citrate buffer solution.

EXAMPLES 57–60

Freeze-dried compositions were obtained in the same manner as that described in Examples 25–28, except for changing the amount of the IFN-α solution (titer: $2 \times 10^7$ IU/ml) from 0.25 ml to 1 ml.

EXAMPLES 61–64

Freeze-dried compositions were obtained in the same manner as that described in Examples 25–28, except for changing the amount of the IFN-α solution (titer: $2 \times 10^7$ IU/ml) from 0.25 ml to 0.01 ml.

EXAMPLES 65–69

Freeze-dried compositions were obtained in the same manner as that described in Examples 1–4, except for changing the amount of sucrose from 40 mg to 25 mg.

EXAMPLES 70–73

Freeze-dried compositions were obtained in the same manner as that described in Examples 1–4, except for changing the amount of sucrose from 40 mg to 80 mg.

EXAMPLES 74–77

Freeze-dried compositions were obtained in the same manner as that described in Examples 25–28, except for using 0.25 ml of IFN-β solution (titer: $2 \times 10^7$ IU/ml) in place of the IFN-α solution.

EXAMPLES 78–81

Freeze-dried compositions were obtained in the same manner as that described in Examples 29–32, except for using 0.25 ml of IFN-β solution (titer: $2 \times 10^7$ IU/ml) in place of the IFN-solution.

EXAMPLES 82–85

Freeze-dried compositions were obtained in the same manner as that described in Examples 33–36, except for using 0.25 ml of an IFN-β solution (titer: $2\times10^7$ IU/ml) in place of the IFN-α solution.

EXAMPLES 86–89

Freeze-dried compositions were obtained in the same manner as that described in Examples 25–28, except for using 0.25 ml of IFN-γ solution (titer: $2\times10^7$ IU/ml) in place of the IFN-α solution.

EXAMPLES 90–93

Freeze-dried compositions were obtained in the same manner as that described in Examples 29–32, except for using 0.25 ml of IFN-γ solution (titer: $2\times10^7$ IU/ml) in place of the IFN-α solution.

EXAMPLES 94–97

Freeze-dried compositions were obtained in the same manner as that described in Examples 25–28, except for using 0.25 ml of erythropoietin solution (titer: $1\times10^5$ IU/ml) in place of the IFN-α solution.

EXAMPLES 98–101

Freeze-dried compositions were obtained in the same manner as that described in Examples 29–32, except for using 0.25 ml of erythropoietin solution (titer: $1\times 10^5$ IU/ml) in place of the IFN-α solution.

EXAMPLES 102–105

Freeze-dried compositions were obtained in the same manner as that described in Examples 25–28, except for using 0.25 ml of G-CSF solution (titer: $1\times10^7$ IU/ml) in place of the IFN-α solution.

EXAMPLES 106–109

Freeze-dried compositions were obtained in the same manner as that described in Examples 29–32, except for using 0.25 ml of G-CSF solution (titer: $1\times10^7$ IU/ml) in place of the IFN-α solution.

Freeze-dried products containing the hydrophobic amino acids obtained in the above Examples 5–109 respectively are capable of effectively suppressing the foamability in redissolving the freeze-dried products and of considerably improving the products' appearances by preventing the freeze-dried cakes from shrinkage.

INDUSTRIAL APPLICABILITY

According to the present invention, foaming typically caused by dissolving dry compositions containing saccharides are effectively inhibited, thereby enabling to prepare a solution excellent in its clarity. Further, even in the case of employing a lyophilization as the drying method, freeze-dried cakes obtained therein are effectively prevented from shrinkage, giving the dry products excellent in the appearances.

In the dry compositions of the invention, especially in the freeze-dried compositions, the moisture content is satisfactorily reduced in a shorter drying time than that required for the conventional freeze-dried products which do not contain any of the hydrophobic amino acids having the hydropathy index of not less than 2. Accordingly, the time required for lyophilization is reduced in the process for preparation of dry compositions as a whole, which is advantageous in the industrial production.

What is claimed is:

1. The foam inhibitor comprising a hydrophobic amino acid having a hydropathy index of not less than 3.8 as an essential component which inhibits foaming induced when dissolving a dry composition containing saccharide.

2. The foam inhibitor according to claim 1, wherein the hydrophobic amino acid has a hydropathy index of 3.8–4.5.

3. The foam inhibitor according to claim 1, wherein the hydrophobic amino acid is at least one member selected from the group consisting of valine, leucine and isoleucine.

4. The foam inhibitor according to claim 1, wherein the hydrophobic amino acid is present in an amount of from 1–100 wt. % based on 100 wt. % of saccharide contained in the dry composition.

5. The foam inhibitor according to claim 4, wherein the saccharide is at least one member selected from the group consisting of sucrose, maltose, lactose, trehalose, mannitol, xylitol, dextran, and chondoroitin sulfate.

6. The foam inhibitor according to claim 1, wherein the dry composition is a freeze-dried composition.

7. A water-soluble dry composition comprising a pharmacologically active proteinaceous substance, a saccharide, and a hydrophobic amino acid having a hydropathy index of not less than 3.8, where the hydrophobic amino acid is present in an amount of from 0.05 wt. % to not more than 40 wt. % based on the total amount of the dry composition.

8. The water-soluble dry composition according to claim 7, wherein the hydrophobic amino acid has a hydropathy index of 3.8–4.5.

9. The water-soluble dry composition according to claim 7, wherein the saccharide is at least one member selected from the group consisting of sucrose, maltose, lactose, trehalose, mannitol, xylitol, dextran and chondoroitin sulfate.

10. The water-soluble dry composition according to claim 7, wherein the pharmacologically active proteinaceous substance is at least one member selected from the group consisting of antiviral polypeptides, immunomodulator polypeptides and hematinic polypeptides.

11. The water-soluble dry composition according to claim 7, wherein the pharmacologically active proteinaceous substance is at least one member selected from the group consisting of antiviral polypeptides, immunomodulator polypeptides and hematinic polypeptides, and the saccharide is at least one member selected from the group consisting of disaccharides, sugar alcohols, and polysaccharides.

12. The water-soluble dry composition according to claim 7, wherein the hydrophobic amino acid is present in an amount of from 1–100 wt. % based on 100 wt. % of saccharide contained in the dry composition.

13. The water-soluble dry composition according to claim 12, wherein the amount of the hydrophobic amino acid is present in an amount of from 0.1–30 wt. % based on the total amount of the dry composition.

14. The water-soluble dry composition according to claim 13, wherein the amount of the hydrophobic amino acid is present in an amount of from 0.1–30 wt. % based on 100 wt. % of the saccharide contained in the dry composition.

15. The water-soluble dry composition according to claim 13, wherein the hydrophobic amino acid is present in the amount of from 0.5–30 wt. % based on the total amount of the dry composition.

16. The water-soluble dry composition according to claim 13, wherein the pharmacologically active proteinaceous substance is at least one member selected from the group consisting of antiviral polypeptides, immunomodulator polypeptides and hematinic polypeptides, and the saccharide is at least one member selected from the group consisting of disaccharides, sugar alcohols, and polysaccharides.

17. The water-soluble dry composition according to claim 16, wherein the pharmacologically active proteinaceous substance is interleukin and/or interferon, and the saccharide is a disaccharide.

18. The water-soluble dry composition according to claim 7, wherein the dry composition is a freeze-dried composition.

19. The water-soluble dry composition according to claim 18, wherein the pharmacologically active proteinaceous substance is at least one member selected from the group consisting of antiviral polypeptides, immunomodulator polypeptides and hematinic polypeptides.

20. The water-soluble dry composition according to claim 19, wherein the pharmacologically active proteinaceous substance is interleukin and/or interferon, and the saccharide is a disaccharide.

21. The water-soluble dry composition according to claim 7, where said composition is substantially free of human serum albumins, and where said composition contains a polar amino acid having a hydropathy index of not more than 0, and a surfactant.

22. The water-soluble dry composition according claim 7, wherein the pharmacologically active proteinaceous substance is interferon-α.

23. The water-soluble dry composition according to claim 17, wherein the pharmacologically active proteinaceous substance is interferon-α.

* * * * *